United States Patent
Kim et al.

(10) Patent No.: US 9,291,571 B2
(45) Date of Patent: Mar. 22, 2016

(54) AMMONIA GAS DETECTION APPARATUS AND A SEMICONDUCTOR FABRICATION LINE INCLUDING THE SAME

(71) Applicant: Samsung Electronics Co., Ltd., Gyeonggi-do (KR)

(72) Inventors: Sungman Kim, Gyeonggi-do (KR); Jin Ha Jeong, Gyeonggi-do (KR); Jongsan Kim, Gyeonggi-do (KR); Ronald Myungsup Shim, Gyeonngi-do (KR)

(73) Assignee: Samsung Electronics Co., Ltd. (KR)

( * ) Notice: Subject to any disclaimer, the term of this patent is extended or adjusted under 35 U.S.C. 154(b) by 458 days.

(21) Appl. No.: 13/713,359

(22) Filed: Dec. 13, 2012

(65) Prior Publication Data

US 2013/0145987 A1 Jun. 13, 2013

(30) Foreign Application Priority Data

Dec. 13, 2011 (KR) ........................ 10-2011-0133766

(51) Int. Cl.

| | |
|---|---|
| *G01N 15/06* | (2006.01) |
| *G01N 33/00* | (2006.01) |
| *G01N 33/48* | (2006.01) |
| *G01N 21/78* | (2006.01) |
| *G01N 21/05* | (2006.01) |

(52) U.S. Cl.
CPC .............. *G01N 21/783* (2013.01); *G01N 21/05* (2013.01)

(58) Field of Classification Search
CPC ........ G01N 15/06; G01N 33/00; G01N 33/48
USPC .............. 422/50, 68.1, 83, 62, 63, 80, 81, 98; 436/43
See application file for complete search history.

(56) References Cited

U.S. PATENT DOCUMENTS

| | | | | |
|---|---|---|---|---|
| 3,649,505 | A * | 3/1972 | Strickler et al. ............... | 204/415 |
| 4,018,660 | A * | 4/1977 | Hansen et al. ................ | 204/417 |
| 4,650,561 | A * | 3/1987 | Robins et al. ................. | 204/416 |
| 5,057,436 | A * | 10/1991 | Ball .............................. | 436/113 |
| 5,234,567 | A * | 8/1993 | Hobbs et al. ................... | 204/415 |
| 5,439,569 | A * | 8/1995 | Carpio ............................ | 134/1.3 |
| 5,445,726 | A * | 8/1995 | Cammann .................... | 205/780.5 |
| 5,494,640 | A * | 2/1996 | Simon et al. ............... | 422/82.05 |

(Continued)

FOREIGN PATENT DOCUMENTS

| | | |
|---|---|---|
| JP | 03-154555 | 7/1991 |
| JP | 10-096699 | 4/1998 |

(Continued)

*Primary Examiner* — Brian J Sines
(74) *Attorney, Agent, or Firm* — Myers Bigel & Sibley, P.A.

(57) ABSTRACT

An ammonia gas detection apparatus includes an ammonia sensor that is configured to detect an ammonia gas in a gas stream and to generate a first output signal when the ammonia gas is detected in the gas stream. The ammonia sensor does not detect the ammonia gas in the gas stream when the gas stream further includes an interference gas that disrupts operation of the ammonia sensor. A discoloration gauge includes a reaction solution that changes from a first color to a second color responsive to exposure to the ammonia gas in the gas stream, regardless of the presence of the interference gas, and a detector that generates a second output signal responsive to the reaction solution changing from the first color to the second color. A communication interface outputs the first and second output signal to a host computer that detects presence of the ammonia gas.

11 Claims, 5 Drawing Sheets

(56) References Cited

U.S. PATENT DOCUMENTS

| | | | |
|---|---|---|---|
| 5,583,282 A * | 12/1996 | Tom | 73/31.03 |
| 5,866,075 A * | 2/1999 | Gupta et al. | 422/88 |
| 5,879,631 A * | 3/1999 | Wewers et al. | 422/98 |
| 6,046,054 A * | 4/2000 | McGeehin et al. | 436/121 |
| 6,051,437 A * | 4/2000 | Luo et al. | 436/172 |
| 6,897,960 B2 | 5/2005 | DiMeo, Jr. et al. | |
| 6,950,589 B2 | 9/2005 | Okuda | |
| 7,198,753 B1 * | 4/2007 | Campbell et al. | 422/68.1 |
| 7,541,586 B2 | 6/2009 | Miller | |
| 2003/0003589 A1 * | 1/2003 | Khalil et al. | 436/113 |
| 2003/0080295 A1 * | 5/2003 | Webber et al. | 250/341.2 |
| 2004/0132202 A1 * | 7/2004 | Nishiyama et al. | 436/113 |
| 2004/0244466 A1 * | 12/2004 | Shen | 73/24.01 |
| 2008/0041136 A1 * | 2/2008 | Kopelman et al. | 73/19.1 |
| 2009/0014330 A1 * | 1/2009 | Sugaya et al. | 204/424 |
| 2013/0062203 A1 * | 3/2013 | Nakano et al. | 204/427 |

FOREIGN PATENT DOCUMENTS

| | | |
|---|---|---|
| JP | 2001-091333 | 4/2001 |
| JP | 2002-048779 | 2/2002 |
| KR | 10-0096282 B1 | 10/1995 |
| KR | 1020010016813 | 3/2001 |
| KR | 2010-0127387 A | 12/2010 |

* cited by examiner

Fig. 6

AMMONIA GAS DETECTION APPARATUS AND A SEMICONDUCTOR FABRICATION LINE INCLUDING THE SAME

CROSS-REFERENCE TO RELATED APPLICATIONS

This U.S. non-provisional patent application claims priority under 35 U.S.C. §119 to Korean Patent Application No. 10-2011-00133766, filed on Dec. 13, 2011, in the Korean Intellectual Property Office, the entire contents of which are hereby incorporated by reference.

BACKGROUND OF THE INVENTION

Embodiments of the inventive concepts relate to systems for managing a semiconductor fabrication line, and more particularly, to apparatus for detecting a leakage of ammonia gas in a semiconductor fabrication line and a system of managing a semiconductor fabrication line including the same.

The semiconductor industry has been identified as a typical high-tech electric/electronic industry. Semiconductor devices are generally fabricated in a very clean fabrication environment. A semiconductor fabrication line generally includes a clean room, in which a semiconductor fabricating apparatus is located. A semiconductor fabricating apparatus may use reaction gases that are poisonous and can be harmful to the human body. Accordingly, a leakage of reaction gas in a semiconductor fabrication line may lead to a serious accident.

To avoid the leakage accident, industrial gas alarms are generally required to be installed in the semiconductor fabrication line. The use of the industrial gas alarm may reduce the serious risks resulting from a leakage of a harmful gas, such as a flammable or toxic gas. For example, ammonia gas may be detected by an ammonia sensor. However, an ammonia sensor, which has been used for a conventional semiconductor fabrication line management system, may not function properly due to the presence of interference gases, thereby reducing productivity of the semiconductor fabrication line.

SUMMARY

Some embodiments of the present invention provide an ammonia gas detection apparatus that includes an ammonia sensor positioned proximate a gas stream that is configured to detect an ammonia gas in the gas stream and to generate a first output signal when the ammonia gas is detected in the gas stream. The ammonia sensor does not detect the ammonia gas in the gas stream when the gas stream further includes an interference gas that disrupts operation of the ammonia sensor. A discoloration gauge is positioned proximate the gas stream that includes a reaction solution that changes from a first color to a second color, different from the first color, responsive to exposure to the ammonia gas in the gas stream, regardless of the presence of the interference gas, and a detector that generates a second output signal responsive to the reaction solution changing from the first color to the second color. A communication interface outputs the first output signal and the second output signal to a host computer that detects presence of the ammonia gas in the gas stream based on the first output signal and the second output signal.

In other embodiments, the reaction solution is phenylboronic acid and the detector is an optical detector. The discoloration gauge includes a tube and a pump coupled to the tube that pumps the gas stream through the tube. A wick or filler in the tube includes the reaction solution therein so that the reaction solution is exposed to the gas stream when the gas stream is pumped through the tube. The wick or filler may be cotton or wadding.

In further embodiments, the discoloration gauge further includes a hole in the tube and a vessel containing the reaction solution coupled to the tube proximate the hole in the tube. The wick or filler is a wick that extends through the hole in the tube into the vessel to contact the reaction solution in the vessel to draw reaction solution from the vessel into a portion of the wick in the tube.

In other embodiments, the wick or filler is a filler and the discoloration gauge further includes at least one membrane positioned on at least one side of the filler in the tube that limits drying out of the reaction solution in the filler when the gas stream is pumped through the tube.

In yet further embodiments, the detector further includes a color filter that preferentially passes light of the second color to the optical detector. The ammonia sensor may include an electrolyte film and a hydrogen electrode. The electrolyte film diffuses the ammonia gas or ammonium ions therein. The hydrogen electrode detects a concentration of hydrogen ions generated by the ammonia gas or ammonium ions therein diffused by the electrolyte film and generates the first output based on the detected concentration.

In yet other embodiments, a semiconductor fabrication line includes detection apparatus described above and further includes the host computer, a fabrication apparatus and an ammonia supply portion. The ammonia supply portion is coupled to the fabrication apparatus and supplies ammonia gas to the fabrication apparatus. The ammonia sensor and the discoloration gauge are positioned proximate the fabrication apparatus of the ammonia supply portion to detect leaks of ammonia gas therefrom.

In further embodiments, the ammonia sensor comprises a first ammonia sensor, the discoloration gauge comprises a first discoloration gauge and the communication interface comprises a first communication interface, all of which are positioned proximate the fabrication apparatus to detect leaks of ammonia gas from the fabrication apparatus. The fabrication line further includes a second ammonia sensor, a second discoloration gauge and a second communication interface, all of which are positioned proximate the ammonia supply portion to detect leaks of ammonia gas from the ammonia supply portion. The host computer is configured to detect leaks of ammonia gas from the fabrication apparatus based on the first output signal and the second output signal from the first interface and to detect leaks of ammonia gas from the ammonia supply portion based on the first output signal and the second output signal from the second apparatus. The fabrication apparatus may be located in a clean room and the ammonia supply portion may be located in a supply room located below the clean room and separated therefrom.

BRIEF DESCRIPTION OF THE DRAWINGS

Example embodiments will be more clearly understood from the following brief description taken in conjunction with the accompanying drawings. FIGS. 1 through 6 represent non-limiting, example embodiments as described herein.

It should be noted that these figures are intended to illustrate the general characteristics of methods, structure and/or materials utilized in certain example embodiments and to supplement the written description provided below. These drawings are not, however, to scale and may not precisely reflect the precise structural or performance characteristics of any given embodiment, and should not be interpreted as defining or limiting the range of values or properties encompassed by example embodiments. For example, the relative thicknesses and positioning of molecules, layers, regions and/or structural elements may be reduced or exaggerated for clarity. The use of similar or identical reference numbers in the various drawings is intended to indicate the presence of a similar or identical element or feature.

DETAILED DESCRIPTION

Advantages and features of the present inventive concept and methods of accomplishing the same may be understood more readily by reference to the following detailed description of preferred embodiments and the accompanying drawings. The present inventive concept may, however, be embodied in many different forms and should not be construed as being limited to the embodiments set forth herein. Rather, these embodiments are provided so that this disclosure will be thorough and complete and will fully convey the concept of the invention to those skilled in the art, and the present inventive concept will only be defined by the appended claims. Like reference numerals refer to like elements throughout the specification.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

It will be understood that when an element or layer is referred to as being "on", "connected to" or "coupled to" another element or layer, it can be directly on, connected or coupled to the other element or layer or intervening elements or layers may be present. In contrast, when an element is referred to as being "directly on", "directly connected to" or "directly coupled to" another element or layer, there are no intervening elements or layers present. Other words used to describe the relationship between elements or layers should be interpreted in a like fashion (e.g., "between" versus "directly between," "adjacent" versus "directly adjacent," "on" versus "directly on"). As used herein, the term "and/or" includes any and all combinations of one or more of the associated listed items.

It will be understood that, although the terms first, second, etc. may be used herein to describe various elements, components, regions, layers and/or sections, these elements, components, regions, layers and/or sections should not be limited by these terms. These terms are only used to distinguish one element, component, region, layer or section from another region, layer or section. Thus, a first element, component, region, layer or section discussed below could be termed a second element, component, region, layer or section without departing from the teachings of the present inventive concept.

Spatially relative terms, such as "beneath", "below", "lower", "above", "upper", and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, the exemplary term "below" can encompass both an orientation of above and below. The device may be otherwise oriented (rotated 90 degrees or at other orientations) and the spatially relative descriptors used herein interpreted accordingly.

Embodiments are described herein with reference to cross-section illustrations that are schematic illustrations of idealized embodiments (and intermediate structures). As such, variations from the shapes of the illustrations as a result, for example, of manufacturing techniques and/or tolerances, are to be expected. Thus, these embodiments should not be construed as limited to the particular shapes of regions illustrated herein but are to include deviations in shapes that result, for example, from manufacturing. For example, an implanted region illustrated as a rectangle will, typically, have rounded or curved features and/or a gradient of implant concentration at its edges rather than a binary change from implanted to non-implanted region. Likewise, a buried region formed by implantation may result in some implantation in the region between the buried region and the surface through which the implantation takes place. Thus, the regions illustrated in the figures are schematic in nature and their shapes are not intended to illustrate the actual shape of a region of a device and are not intended to limit the scope of the present inventive concept.

Unless otherwise defined, all terms (including technical and scientific terms) used herein have the same meaning as commonly understood by one of ordinary skill in the art to which the present inventive concept belongs. It will be further understood that terms, such as those defined in commonly used dictionaries, should be interpreted as having a meaning that is consistent with their meaning in the context of the relevant art and this specification and will not be interpreted in an idealized or overly formal sense unless expressly so defined herein.

Figure 1:
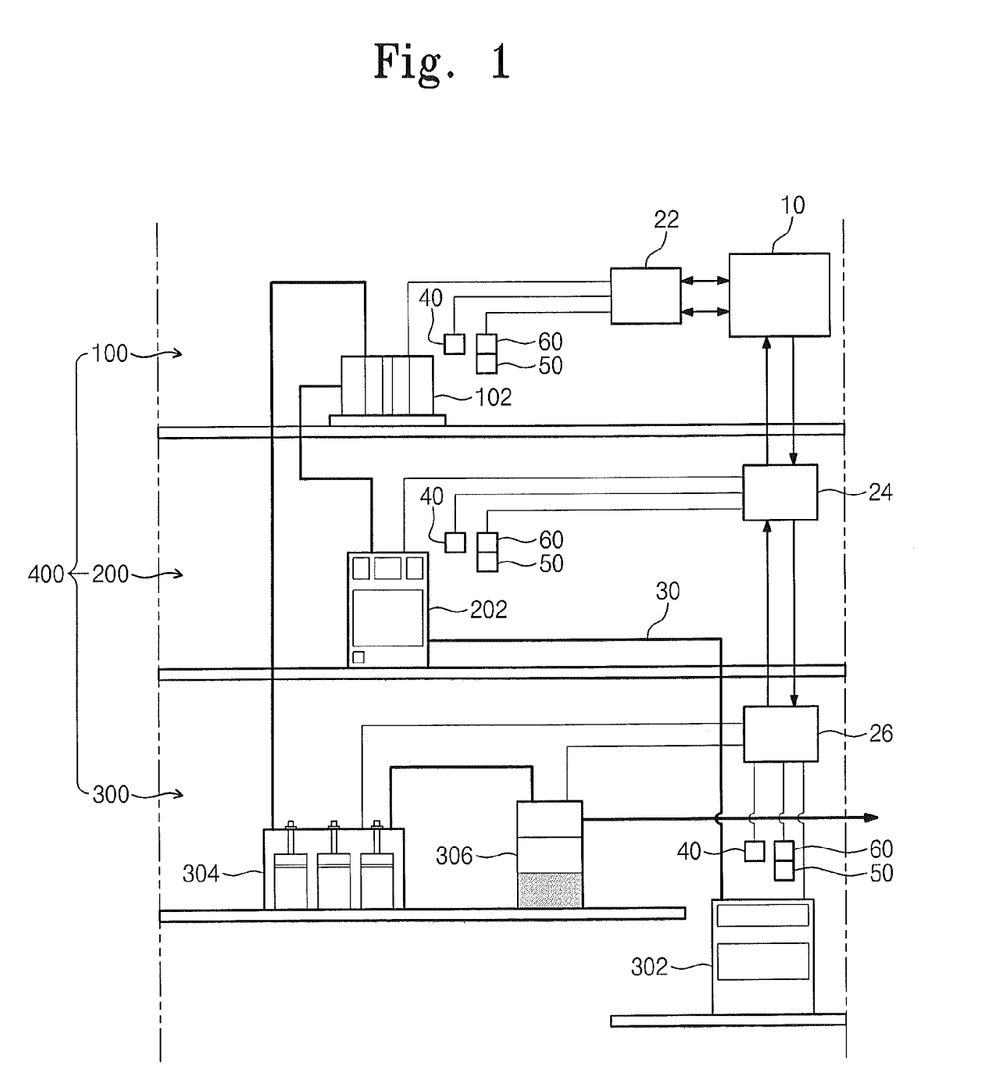
FIG. 1 is a schematic diagram of a semiconductor fabrication line including a management system of a semiconductor fabrication line according to some embodiments of the inventive concept.
Figure 2:
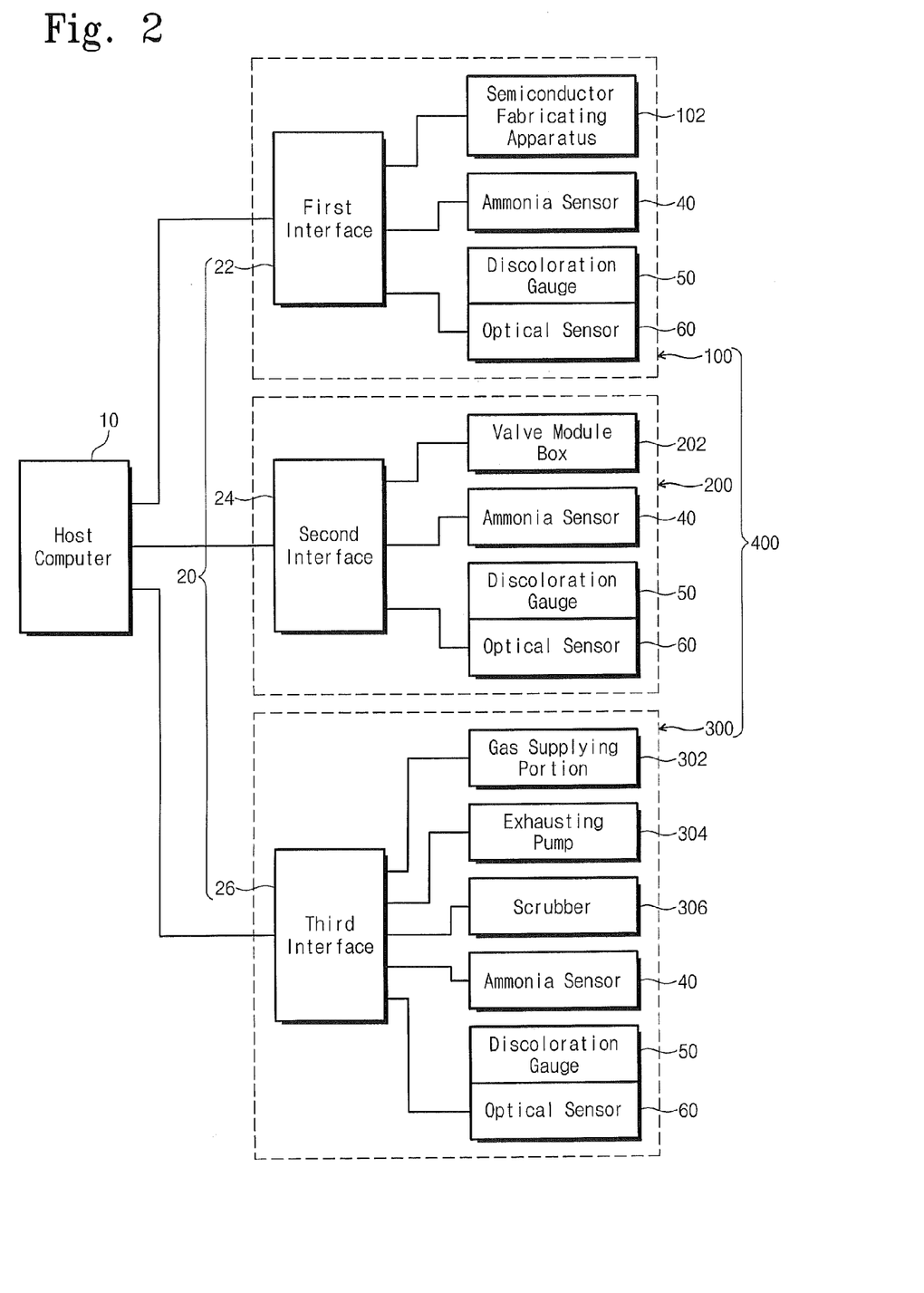
FIG. 2 is a block diagram of the management system of FIG. 1.

Hereinafter, example embodiments will be explained in detail with reference to the accompanying drawings. FIG. 1 is a schematic diagram of a management system of a semiconductor fabrication line according to example embodiments of the inventive concept. FIG. 2 is a simplified block diagram of the system of FIG. 1.

Referring to FIGS. 1 and 2, a fabrication management system according to example embodiments of the inventive concept may include at least one discoloration gauge 50 and at least one optical sensor 60. The discoloration gauge 50 may include a portion whose color may be changed by ammonia gas leaked from a semiconductor fabrication line 400, and the optical sensor 60 may be configured to monitor a change in color of the discoloration gauge 50. In example embodiments, the discoloration gauge 50 and the optical sensor 60 may be used to detect the ammonia gas, in complementary conjunction with at least one ammonia sensor 40. The discoloration gauges 50 may increase reliability in detecting the ammonia gas, for example, in a situation where an interference gas in the gas from the fabrication line being monitored causes a detection error by the ammonia sensor 40. In other words, the discoloration gauge 50 may detect an ammonia gas leakage that was not detected by the ammonia sensor 40. As such, some embodiments may increase productivity of the fabrication management system/fabrication line.

A host computer 10 may manage or control the overall process of the semiconductor fabrication line 400. For example, the host computer 10 may be configured to monitor an ammonia gas leaked in the semiconductor fabrication line 400. In the case in which the ammonia gas is leaked, an ammonia detection signal from the ammonia sensors 40 and the optical sensors 60 may be transferred to the host computer 10 via interfaces 20. The interfaces 20 may include first to third interface 22, 24, and 26. The discoloration gauges 50 and the optical sensors 60 may be provided proximate to the ammonia sensors 40 to detect a same gas stream. As such, as used herein in this context, proximate refers to positioned to detect gases in a same gas stream. The discoloration gauges 50 and the optical sensors 60 may be provided in pairs.

In example embodiments, the ammonia sensors 40 and the discoloration gauges 50 may be configured to detect ammonia gas. Here, not only the ammonia gas but also the interference gas(es) in the semiconductor fabrication line 400 may produce the ammonia detection signal from the ammonia sensors 40. In other words, the interference gas may limit the ability of the ammonia sensors 40 to detect ammonia gas in the gas flow being monitored as both the interference gas and the ammonia gas may be in the monitored gas flow. However, the discoloration gauge 50 may be configured to detect selectively the ammonia gas regardless of the presence of the interference gases. As described above, the discoloration gauge 50 and the optical sensor 60 may provide increase reliability in detecting the ammonia gas even in situations provided with an interference gas that may also be leaked from the semiconductor fabrication line 400. Accordingly, in some embodiments, even if the ammonia sensors 40 are disturbed by the interference gas, the host computer 10 can correctly monitor a leak of ammonia gas based on the ammonia detection signal from the optical sensors 60. In addition, this arrangement may enable the operators in the semiconductor fabrication line 400 to perceive a leakage of ammonia gas correctly and quickly.

The semiconductor fabrication line 400 may include a clean room 100, a gas conduit valve room 200, and a gas supplying room 300. The clean room 100 may be an isolated space, in which the number of particle and a concentration of ammonia gas are controlled to be under predetermined levels, respectively. At least one semiconductor fabricating apparatus 102 may be located in the clean room 100. For example, the semiconductor fabricating apparatus 102 may be a chemical or physical vapor deposition apparatus, in which ammonia gas is used as a part of a source gas. The ammonia sensor 40 and the discoloration gauge 50 may be provided near the semiconductor fabricating apparatus 102. This is because the ammonia gas may be generally leaked at the semiconductor fabricating apparatus 102 or at a fitting portion between the semiconductor fabricating apparatus 102 and a conduit 30. If there is a leakage of ammonia gas, a color of the discoloration gauge 50 may be changed. The optical sensors 60 may produce a detection signal in response to the change in color of the discoloration gauge 50. The detection signal may be transferred to the host computer 10 via, for example, the first interface 22. On the basis of this detection signal, the fact that the leakage of ammonia gas occurs in the clean room 100 can be detected by the host computer 10.

In example embodiments, the gas conduit valve room 200 may be disposed below the clean room 100. A valve module box 202 may be provided in the gas conduit valve room 200 to surround valves controlling a flow of the ammonia gas through the conduit 30. An air cleaning system may be further be provided in the gas conduit valve room 200. Similarly, the ammonia sensor 40 and the discoloration gauge 50 may be provided proximate to the valve module box 202. On the basis of detection signals transferred from the ammonia sensor 40 and the optical sensor 60 proximate the valve module box 202 via the second interface 24, the host computer 10 may determine whether a leakage of ammonia gas occurs in the gas conduit valve room 200.

The gas supplying room 300 may be provided below the gas conduit valve room 200. A gas supplying portion 302, an exhausting pump 304, and a scrubber 306 may be provided in the gas supplying room 300. The gas supplying portion 302 may include an ammonia gas tank. The gas supplying portion 302 may be configured to supply the ammonia gas to the valve module box 202 and the semiconductor fabricating apparatus 102 at a constant pressure. The exhausting pump 304 may pump out the ammonia gas and/or post reaction gases from the semiconductor fabricating apparatus 102. The scrubber 306 may be configured to purify or remove the ammonia gas and/or the post reaction gas and exhaust them into the air. The ammonia sensor 40, the discoloration gauge 50, and the optical sensor 60 may be disposed proximate to at least one of the gas supplying portion 302, the exhausting pump 304, or the scrubber 306. If there is a leakage of ammonia gas, a color of the discoloration gauge 50 may be changed. The optical sensor 60 may produce a detection signal in response to the change in color of the discoloration gauge 50. On the basis of detection signals transferred from the ammonia sensor 40 and the optical sensors 60 in the gas supplying room 300 via the third interface 26, the host computer 10 may determine whether a leakage of ammonia gas occurs in the gas supplying room 300. Here, the use of both of the discoloration gauge 50 and the optical sensor 60 may contribute to increase reliability in detecting the ammonia gas, compared with the case of using solely the ammonia sensor 40. As a result, it may be possible to increase productivity of the fabrication management system. In some embodiments, the ammonia sensors 40, discoloration gauges 50 and optical sensors 60, respectively, in each room 100, 200, 300 may be substantially identical.

Figure 3:
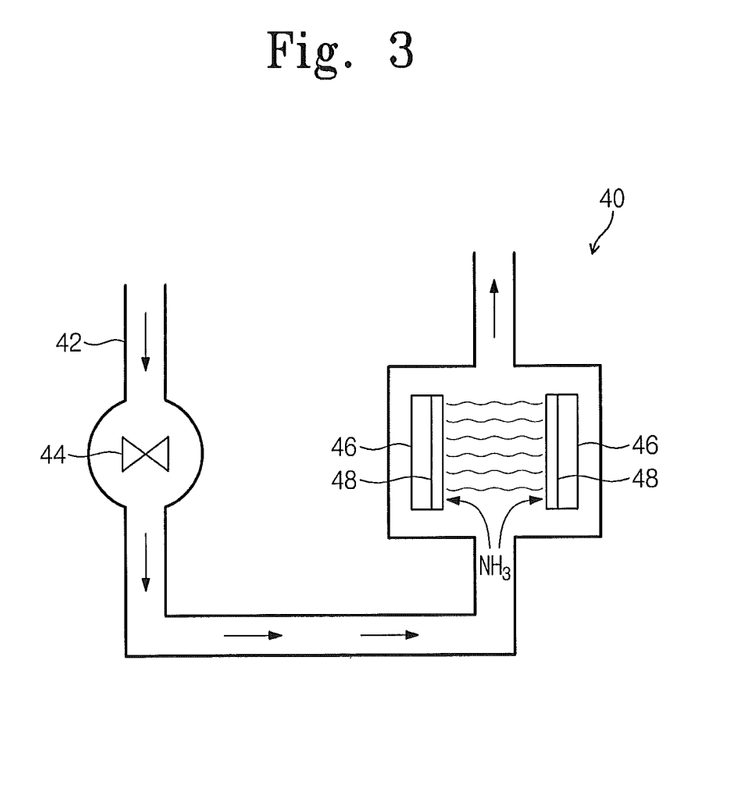
FIG. 3 is a schematic diagram of the ammonia sensor of the system of FIGS. 1 and 2 according to some embodiments.

FIG. 3 is a schematic diagram of the ammonia sensor 40 according to some embodiments. Referring to FIG. 3, the ammonia sensor 40 may include electrolyte films 48 diffusing ammonia gas or ammonium ions contained in the air and hydrogen electrodes 46 used to monitor a variation in hydrogen ion concentration, which may result from the ammonia gas or the ammonium ions diffused from the electrolyte films 48. The electrolyte films 48 may be formed of a material allowing permeation of the ammonia gas or the ammonium ion. In the electrolyte films 48, the ammonia gas may be transformed into ammonium ions. Furthermore, hydrogen ions may be produced during the process, in which the ammonia gas is chemically transformed into the ammonium ions. A potential difference caused by the variation in hydrogen ion concentration may produce an electric current in the hydrogen electrodes 46. The level of this electric current may be detected as presence or absence of ammonia gas in the ammonia sensor 40. In FIG. 3, the arrows in a first tube 42 denote a flow of an ammonia-containing gas across the electrolyte films 48 caused by a first pump 44.

In some cases, some reaction gases other than the ammonia gas may result in a malfunction (e.g., failure to detect the presence of the ammonia gas in the gas stream) of the ammonia sensor 40. For example, interference gases, such as hydrogen ($H_2$) gas or methane gas, may result in the malfunction of the ammonia sensor 40. For all that, according to example embodiments of the inventive concept, even when the interference gas is present, the presence of the ammonia gas may be correctly detected by the discoloration gauge 50 and the optical sensor 60. This is because the discoloration gauge 50 may be configured to include a reaction solution, whose color may be changed by coming into contact with the ammonia gas. According to the way of supplying the reaction solution, the discoloration gauge 50 may be classified into two types: vessel type and non-vessel type. Hereinafter, the discoloration gauge 50 and the optical sensor 60 according to some embodiments will be described in more detail.

Figure 4:
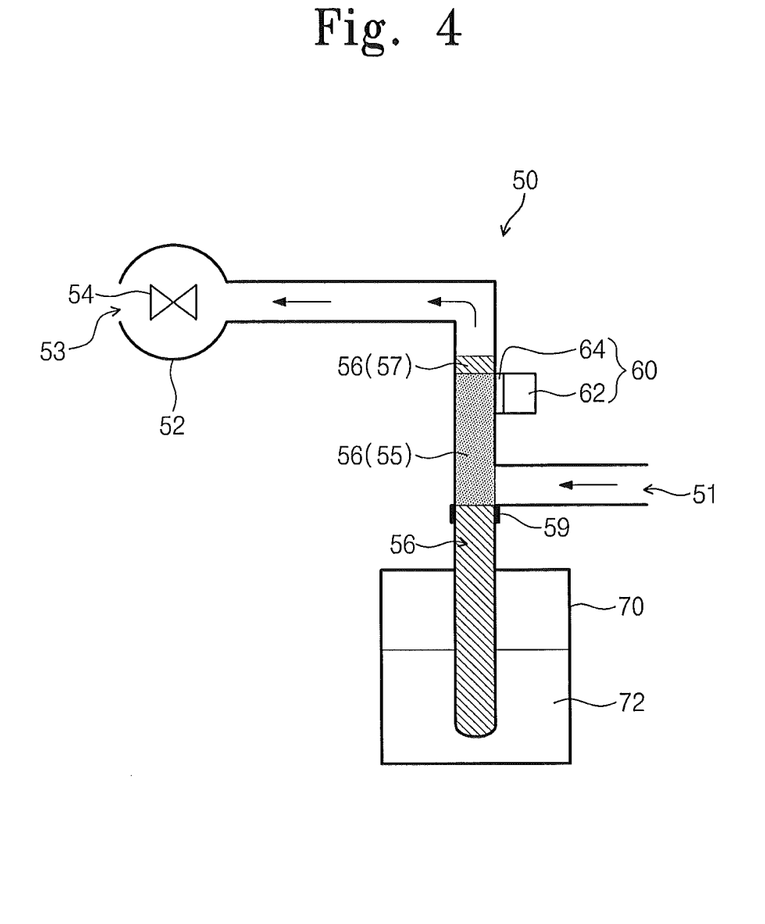
FIG. 4 is a schematic diagram of a discoloration gauge of vessel type and an optical sensor according to some embodiments of the inventive concept.

FIG. 4 is a schematic diagram of a discoloration gauge of vessel type and an optical sensor according to example embodiments of the inventive concept. Referring to FIG. 4, a discoloration gauge 50 of vessel type may include a wick 56 delivering a reaction solution 72 from a vessel 70 to a second tube 52. The wick 56 may be configured to connect the reaction solution 72 in the vessel 70 to the second tube 52. The wick 56 may extend into an inner portion of the second tube 52. The wick 56 may be maintained wetted with the reaction solution 72. The wick 56 may include a white fabric or a white wadding. The vessel 70 may store the reaction solution 72. The vessel 70 may be disposed below the second tube 52. A second pump 54 may be configured to induce a pumping pressure to be used to deliver the air from an inlet 51 of the second tube 52 to an outlet 53 of the second tube 52. The wick 56 may limit the flow of the air in the second tube 52. The second tube 52 may be provided with a hole 59, through which the wick 56 can be passed. Due to the presence of the hole 59, the vessel 70 may be operatively coupled to the second tube 52. Accordingly, the reaction solution 72 stored outside the second tube 52 can be supplied into the discoloration gauge 50 through the wick 56.

The reaction solution 72 may be of a selected material that is discolored when ammonia gas is contained in the air passing through the second tube 52 and exposed to the portion of the wick 56 within the second tube 52 and saturated with the reaction solution 72. The reaction solution 72 may include, for example, a phenylboronic acid. The normal color of the phenylboronic acid may be yellow. The phenylboronic acid may be discolored by reacting with the ammonia gas. Boron ions $B^{3+}$ in the phenylboronic acid may be bonded with nitrogen atoms in the ammonia gas, thereby forming boron nitride. The normal color of the boron nitride may be purple. Accordingly, if the reaction solution 72 is exposed to the ammonia gas, its color may be changed from yellow to purple (i.e., discolored). In this case, the wick 56 wetted with the reaction solution 72 may include a discolored region 55 exposed to the ammonia gas and an original color region 57 not exposed to the ammonia gas.

The optical sensor 60 may be disposed adjacent to the second tube 52 of the discoloration gauge 50. The optical sensor 60 may be configured to detect a change in color of the discoloration gauge 50 caused by the change in color of the discolored region 55 of the wick 56 therein. For example, the optical sensor 60 may include a light receiving device 62 sensing a visible light from the wick 56 and the reaction solution 72, and a color filter 64 removing a noise from the visible light. The color filter 64 may be configured to filter out a light band, whose wavelength corresponds to the normal (not exposed to ammonia gas) color of the reaction solution 72. A light whose wavelength corresponds to the changed (exposed to ammonia gas) color of the reaction solution 72 may be passed through the color filter 64 and delivered to the light receiving device 62. For example, the color filter 64 may include a purple plastic plate or film, which may remove a yellow light and pass a purple light.

The light receiving device 62 may generate a detection signal, which may be dependent on an intensity of a light passing through the color filter 64. For example, the light receiving device 62 may include a CMOS sensor or a CCD sensor. The light receiving device 62 may be configured to receive a visible light from substantially any source and need not be a special source associated specifically with the gauge 50, such as ambient light which may be emitted from a lighting source located somewhere in the semiconductor fabrication line 400 that is received and reflected from the wick 56. A specific light emitting device may be provided at other side of the second tube 52 to face the light receiving device 62 in some embodiments. The light emitting device may be configured to provide a visible light reflected by or passing through the wick 56. The light emitting device may include a lamp or a light-emitting diode. In either case, the optical sensor 60 may detect a change in color of the discoloration gauge 50.

Figure 5:
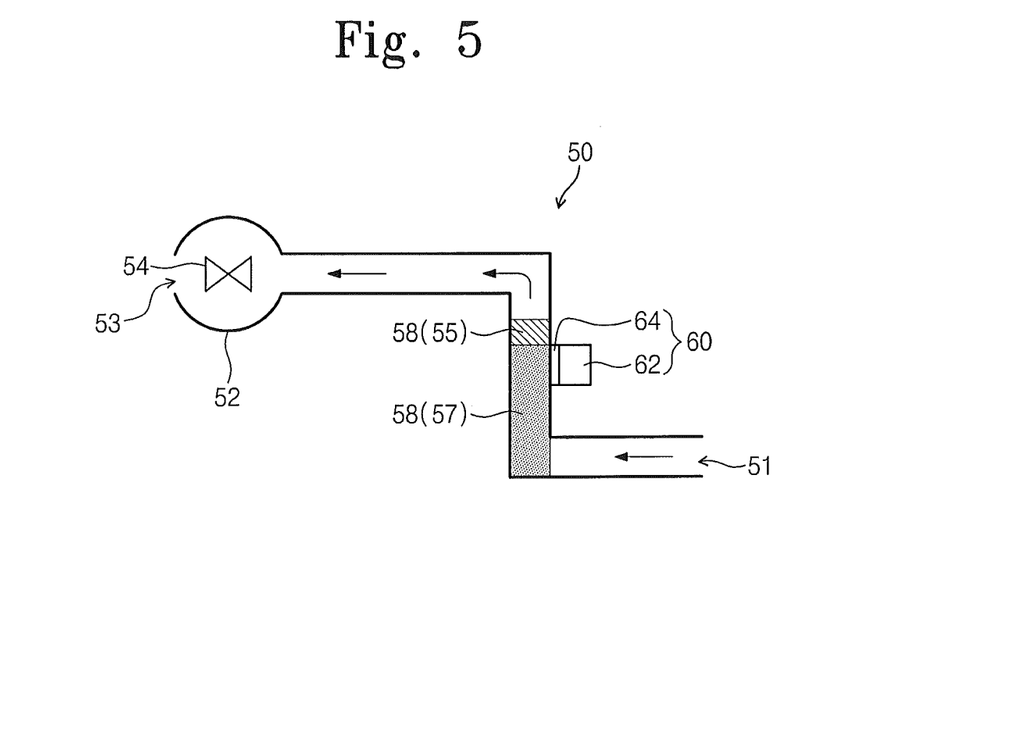
FIGS. 5 and 6 are schematic diagrams illustrating a discoloration gauge of non-vessel type and an optical sensor according to some embodiments of the inventive concept.
Figure 6:
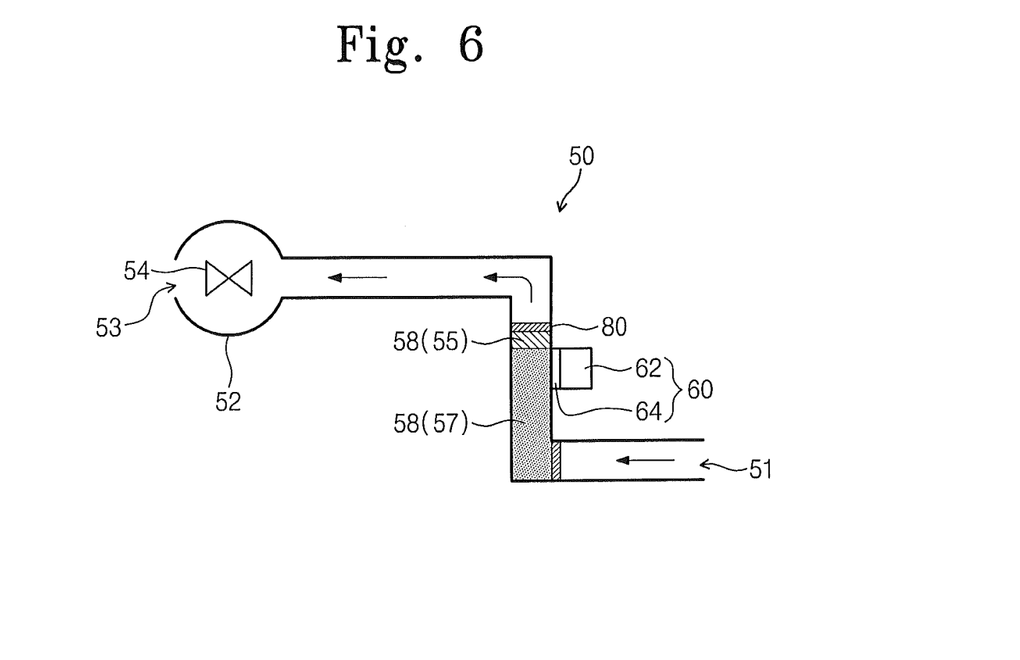

FIGS. 5 and 6 are diagrams illustrating a discoloration gauge of non-vessel type and an optical sensor according to example embodiments of the inventive concept. Referring to FIGS. 5 and 6, the discoloration gauge 50 of non-vessel type may include the second tube 52, the second pump 54 pumping air in the second tube 52, and a filler 58 wetted with the reaction solution 72. The filler 58 may be disposed to fill the second tube 52 and the reaction solution 72 may be discolored by ammonia gas in the air. The filler 58 may include a wick, such as a cotton or a wadding. The reaction solution 72 may be discolored by ammonia gas in the air flowed into the second tube 52. A normal color of the discoloration gauge 50 of non-vessel type may be changed by the ammonia gas. In this case, the filler 58 wetted with the reaction solution 72 may include a discolored region 55 exposed to the ammonia gas and an original color region 57 not exposed to the ammonia gas. The discolored region 55 and the original color region 57 may be continuously changed according to a flow direction of the ammonia gas through the second tube 52. As described above, the reaction solution 72 may include phenylboronic acid.

The reaction solution 72 may be evaporated depending on a flowing speed of the air in the second tube 52. As seen in the embodiments of FIG. 6, membranes 80 may be provided to minimize the evaporation of the reaction solution 72. The membranes 80 may be disposed in the second tube 52 and at both sides of the filler 58. The membranes 80 may reduce a flow speed of the air in the second tube 52. Accordingly, the discoloration gauge 50 of a non-vessel type may have a lifetime increased by the membranes 80. In some embodiments, an injector may be provided in the second tube 52 or in the filler 58 to supply the reaction solution 72.

The optical sensor 60 may be configured to detect a discoloration of the reaction solution 72 in the filler 58. The optical sensor 60 may be provided adjacent to the second tube 52. The optical sensor 60 may include the light receiving device 62, which may be configured to sense a visible light from the filler 58 and the reaction solution 72, and the color filter 64 removing a noise light wavelength different from a changed color wavelength of the reaction solution 72. The light receiving device 62 may generate a detection signal, which may be dependent on an intensity of a light passing through the color filter 64. The color filter 64 may be configured to remove a yellow light and pass a purple light. Accordingly, the discoloration gauge 50 of non-vessel type and the optical sensor 60 may be configured to detect the ammonia gas, regardless of the presence of the interference gases.

As a result, it may be possible to increase productivity of the fabrication management system.

According to example embodiments of the inventive concept, the ammonia gas detection apparatus may include a discoloration gauge selectively sensing ammonia gas even in the presence of interference gases that limit sensitivity of an ammonia sensor and an optical sensor sensing a change in color of the discoloration gauge. The ammonia sensor may be configured to detect a concentration of hydrogen ions, which may be generated from ammonia gases or ammonium ions. The discoloration gauge may include a reaction solution containing phenylboronic acid, and the phenylboronic acid may contain boron ions to be reacted with nitrogen atoms of the ammonia gas. Due to the use of the discoloration gauge and the optical sensor, it is possible to increase reliability in detecting the ammonia gas. This may enable increased productivity using the system of managing a semiconductor fabrication line and/or the ammonia gas detection apparatus used for the same.

As described above, embodiments of the inventive concepts provide an ammonia gas detection apparatus allowing to reduce confusion caused by malfunction of an ammonia sensor and a semiconductor fabrication line management system including the same.

Other example embodiments of the inventive concept provide an ammonia gas detection apparatus allowing to increase productivity of a semiconductor fabrication line and a semiconductor fabrication line management system including the same.

According to example embodiments of the inventive concepts, an ammonia gas detection apparatus may include a host computer, an interface connected to the host computer, an ammonia sensor sensing ammonia gas and generating a first detection signal transferred to the host computer via the interface, a discoloration gauge disposed adjacent to the ammonia sensor to selectively detect the ammonia gas in a situation provided with interference gases causing malfunction of the ammonia sensor, the discoloration gauge detecting complementarily the ammonia gas in conjunction with the ammonia sensor and including a reaction solution to be discolored by the ammonia gas, and an optical sensor sensing a change in color of the discoloration gauge and generating a second detection signal to be transferred to the host computer via the interface.

In example embodiments, the reaction solution of the discoloration gauge may include phenylboronic acid.

In example embodiments, the discoloration gauge may include a tube, a pump pumping the air in the tube, and a wick or a filler wetted by the reaction solution and filling a portion of the tube.

In example embodiments, the wick or the filler may include a cotton or a wadding.

In example embodiments, the tube may include an inlet provided for an inflow of the air, an outlet provided for an outflow of the air, and a hole provided between the outlet and the inlet to draw out a portion of the wick from the tube.

In example embodiments, the device may further include a vessel connected to the tube via the hole to store the reaction solution.

In example embodiments, the device may further include at least one membrane provided at least one of both sides of the wick or the filler disposed in the tube.

In example embodiments, the optical sensor may include a light receiving device sensing an external light or a light reflected from the wick or filler wetted by the reaction solution.

In example embodiments, the optical sensor may include a color filter removing a noise of the light receiving device.

In example embodiments, the ammonia sensor may include an electrolyte film diffusing the ammonia gas or ammonium ions, and a hydrogen electrode detecting a change in concentration of hydrogen ions generated by the ammonia gas or the ammonium ions.

The foregoing is illustrative of the present inventive concept and is not to be construed as limiting thereof. Although a few embodiments of the present inventive concept have been described, those skilled in the art will readily appreciate that many modifications are possible in the embodiments without materially departing from the novel teachings and advantages of the present inventive concept. Accordingly, all such modifications are intended to be included within the scope of the present inventive concept as defined in the claims. Therefore, it is to be understood that the foregoing is illustrative of the present inventive concept and is not to be construed as limited to the specific embodiments disclosed, and that modifications to the disclosed embodiments, as well as other embodiments, are intended to be included within the scope of the appended claims. The present inventive concept is defined by the following claims, with equivalents of the claims to be included therein.

What is claimed is:

1. An ammonia gas detection apparatus, comprising:
   an ammonia sensor positioned proximate a gas stream that is configured to detect an ammonia gas in the gas stream and to generate a first output signal when the ammonia gas is detected in the gas stream;
   a discoloration gauge positioned proximate the gas stream that includes a reaction solution that changes from a first color to a second color, different from the first color, responsive to exposure to the ammonia gas in the gas stream, regardless of a presence of an interference gas, and a detector that generates a second output signal responsive to the reaction solution changing from the first color to the second color, wherein the discoloration gauge comprises:
   a tube;
   a pump coupled to the tube that pumps the gas stream through the tube; and
   a wick or a filler in the tube that includes the reaction solution therein so that the reaction solution is exposed to the gas stream when the gas stream is pumped through the tube; and
   a communication interface that outputs the first output signal and the second output signal to a host computer that detects presence of the ammonia gas in the gas stream based on the first output signal and the second output signal.

2. The detection apparatus of claim 1, wherein the reaction solution comprises phenylboronic acid and the detector comprises an optical detector.

3. The detection apparatus of claim 2, wherein the discoloration gauge further comprises:
   a hole in the tube; and
   a vessel containing the reaction solution coupled to the tube proximate the hole in the tube, wherein the wick or filler comprises a wick that extends through the hole in the tube into the vessel to contact the reaction solution in the vessel to draw the reaction solution from the vessel into a portion of the wick in the tube.

4. The detection apparatus of claim 2, wherein the wick or filler comprises a filler and wherein the discoloration gauge further comprises at least one membrane positioned on at least one side of the filler in the tube that limits drying out of the reaction solution in the filler when the gas stream is pumped through the tube.

5. The detection apparatus of claim 2, wherein the detector further comprises a color filter that preferentially passes light of the second color to the optical detector.

6. The detection apparatus of claim 2, wherein the ammonia sensor comprises:
    an electrolyte film that diffuses the ammonia gas or ammonium ions therein; and
    a hydrogen electrode that detects a concentration of hydrogen ions generated by the ammonia gas or ammonium ions therein diffused by the electrolyte film and generates the first output based on the detected concentration.

7. The detection apparatus of claim 2, wherein the wick or filler comprises cotton or wadding.

8. A semiconductor fabrication line comprising the detection apparatus of claim 2 and further comprising:
    the host computer coupled to the communication interface to receive the first and second output signals;
    a fabrication apparatus controlled by the host computer; and
    an ammonia supply portion coupled to the fabrication apparatus that supplies ammonia gas to the fabrication apparatus, wherein the ammonia sensor and the discoloration gauge are positioned proximate the fabrication apparatus to detect leaks of ammonia gas therefrom.

9. The semiconductor fabrication line of claim 8, wherein the ammonia sensor comprises a first ammonia sensor, the discoloration gauge comprises a first discoloration gauge and the communication interface comprises a first communication interface, all of which are positioned proximate the fabrication apparatus to detect leaks of ammonia gas from the fabrication apparatus and wherein the fabrication line further comprises a second ammonia sensor, a second discoloration gauge and a second communication interface, all of which are positioned proximate the ammonia supply portion to detect leaks of ammonia gas from the ammonia supply portion and wherein the host computer is configured to detect leaks of ammonia gas from the fabrication apparatus based on output signals from the first communication interface and to detect leaks of ammonia gas from the ammonia supply portion based on output signals from the second communication interface.

10. The semiconductor fabrication line of claim 9, wherein the fabrication apparatus is located in a clean room and the ammonia supply portion is located in a supply room located below the clean room and separated therefrom.

11. The detection apparatus of claim 1, wherein the detector comprises an optical sensor comprising a light receiving device sensing an external light or a light reflected from the wick or the filler including the reaction solution.

* * * * *

UNITED STATES PATENT AND TRADEMARK OFFICE
CERTIFICATE OF CORRECTION

PATENT NO. : 9,291,571 B2
APPLICATION NO. : 13/713359
DATED : March 22, 2016
INVENTOR(S) : Kim et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 465 days.

Signed and Sealed this
Fifth Day of July, 2016

Michelle K. Lee
*Director of the United States Patent and Trademark Office*